United States Patent [19]

Martelly et al.

[11] Patent Number: 5,771,899
[45] Date of Patent: Jun. 30, 1998

[54] PESSARY

[75] Inventors: Peter D. Martelly, Swansea, Mass.; Denis Dorsey, Levittown, Pa.

[73] Assignee: Bioteque America Inc., Langhorne, Pa.

[21] Appl. No.: 615,906

[22] Filed: Mar. 14, 1996

[51] Int. Cl.$^6$ ........................................... A61F 6/06
[52] U.S. Cl. ............................................ 128/830; 128/834
[58] Field of Search ..................... 128/830–841

[56] References Cited

U.S. PATENT DOCUMENTS

| | | | |
|---|---|---|---|
| 21,189 | 8/1858 | Elmer | 128/834 |
| 89,647 | 5/1869 | Fraser | 128/834 |
| 288,140 | 11/1883 | Turver | 128/834 |
| 2,404,384 | 7/1946 | Kurkjian | 128/835 |
| 2,638,039 | 5/1953 | Bucky. | |
| 3,646,929 | 3/1972 | Bonnar. | |
| 4,823,814 | 4/1989 | Drogendijk et al. . | |
| 4,895,170 | 1/1990 | Tlapek | 128/837 |
| 4,920,986 | 5/1990 | Biswas. | |
| 5,007,894 | 4/1991 | Enhorning. | |
| 5,224,494 | 7/1993 | Enhorning. | |

FOREIGN PATENT DOCUMENTS 0274762  7/1988  European Pat. Off. .
1115727  5/1968  United Kingdom .

Primary Examiner—Michael A. Brown
Attorney, Agent, or Firm—Caesar, Rivise, Bernstein, Cohen & Pokotilow, Ltd.

[57] ABSTRACT

A pessary for treating uterine prolapse and/or stress urinary incontinence. A first embodiment of the pessary basically comprises a base ring, a sling support, and a sling membrane wall secured together to form an integral unit. The unit is formed of a biocompatible, flexible material, e.g., medical grade silicone, so that it can be collapsed or folded. The base ring is annular member defining a plane. The sling support is an arcuate portion of a ring having a pair of ends secured to the base ring so that the sling support is oriented in a plane extending at an acute angle, e.g., 33 degrees, to the plane of the base ring. The sling membrane is supported between a portion of the base member and a portion of the sling support to forms an arcuate wall of the periphery of the pessary. When the pessary is in place the sling wall presses against the inter-vaginal wall, thereby gently closing the urethra. At the same time the ring base member provides support for the uterus, preventing further migration or prolapse. A second embodiment of the pessary is identical to the first embodiment but includes an additional membrane or wall to provide additional support useful for treating greater degrees of uterine prolapse than the first embodiment.

18 Claims, 3 Drawing Sheets

PESSARY

BACKGROUND OF THE INVENTION

This invention relates generally to medical devices, and more particularly to pessaries.

As is known, the relaxation of pelvic tissue may result in a prolapse of either the uterus, bladder, rectum, or intestines and the result can also cause stress incontinence. Surgery can effectively control the condition but if the patient is elderly or for other reasons a poor operative risk, a physician may consider the use of a vaginal pessary. A pessary that is used as a prolapse device must be as large as possible to be an effective barrier to prevent any internal organs from protruding through the introitus. For some women, who are candidates for the vaginal pessary, a narrow introitus may make the insertion of a pessary quite painful.

For decades various prolapse type devices have been used. They have varied greatly in utility, size, shape, and material composition. In the recent past, pessaries have been made of solid materials such as polypropylene, styrene, acrylic, and even wood. By necessity, these early devices had to be large enough to adequately function as an effective device, but small enough to be inserted through the introitus. Therefore, the selection process of choosing the appropriate pessary for the patient became a relatively difficult task for the physician. These early types of rigid pessaries were simply painful to insert, sometimes painful to "wear", and usually difficult to remove for cleaning purposes.

As improved materials, especially silicone, became available to the medical manufacturers and high-temperature molding techniques improved, innovative and novel pessaries soon appeared that could be flexed and folded for ease of insertion and removal. In fact, even inflatable type pessaries were introduced to the marketplace.

Silicone pessaries are now available in a wide variety of shapes and sizes to control various degrees of prolapse or urinary stress incontinence.

A vaginal pessary designed for the control of urinary incontinence also needs to be as large as possible to be effective device. To avoid painful introitus insertion and vaginal removal problems, several inflatable pessaries have been developed to control urinary stress incontinence. For example, U.S. Pat. No. 5,007,894 discloses an inflatable oval shaped inflatable ring with two strategically placed parallel protrusions that are positioned on either side of the urethra. The inflatable ring simply provides a mechanical platform for the protrusions and also prevents direct pressure from being exerted on the urethra. This pessary, with the exception of the protrusions used to control urinary incontinence, is similar to prior art devices used to control a vaginal prolapse.

Other prior art prolapse devices have been developed to control urinary incontinence and have inflatable portions. Examples of the same are found in U.S. Pat. Nos. 3,646,929, 2,638,039, 4,823,814, 4,920,986, and 5,224,494, in British Patent No. 1,115,727, and in European Patent Application 0274762. All of these pessaries, except U.S. Pat. No. 5,224,494, have a tube that extends out of the vagina to control inflation but the tubes can cause a great deal of discomfort to the patient. For example, U. S. Pat. No. 5,224,494 discloses a device that has a tube required for inflation but the pessary has a platform to hold the tube within the vagina after inflation. However, the tube and platform may block normal vagina secretions. U.S. Pat. No. 4,823,814 discloses a ring-like pessary for treating prolapses of internal female sex organs and for relieving urinary incontinence. The pessary basically comprises a deformable ring which can be bent by hand into any desired shape and its circumferential dimension can be increased or decreased by hand. In order to control incontinence the pessary includes an inflatable portion in the ring which is coupled via a tube to an exteriorly located balloon.

Although inflatable pessaries are available, they have not been widely accepted because of the obvious problems associated with these devices. Clearly, a pessary intended to control urinary incontinence and/or the prolapse of the uterus must be easily inserted and removed for cleaning, cause no discomfort to the patient, and be virtually unnoticed by the patient once the device has been inserted.

While the devices disclosed in the aforementioned prior art patents and application may be generally suitable for their intended purposes, they never the less appear to leave much to be desired from various standpoints, such as simplicity of construction, ease of insertion, removal, and use, effectiveness, comfort, concealability.

OBJECTS OF THE INVENTION

Accordingly, it is a general object of this invention to provide a pessary which overcomes the disadvantages of the prior art.

It is another object of this invention to provide a vaginal pessary which is effective for treating prolapse and incontinence.

It is another object of this invention to provide a vaginal pessary that is easy to insert and remove.

It is another object of this invention to provide a vaginal pessary which can be worn comfortably.

It is still a further object of this invention to provide a vaginal pessary that can be readily folded or collapsed to a relatively small size for insertion, and when released, after insertion, automatically assumes its natural shape for providing the necessary comfort and control for the patient.

It is another object of this invention to provide a vaginal pessary which is simple in construction.

SUMMARY OF THE INVENTION

These and other objects of this invention are achieved by providing a pessary for treating uterine prolapse and/or stress urinary incontinence. The pessary is formed of a biocompatible material, e.g., medical grade silicone, and basically comprises a base member, a sling support member, and a sling wall member.

The base member is in the form of a ring, e.g., an annular ring, defining a plane. The sling member is in the form of an arcuate portion of a ring and has a pair of ends. The sling support member is disposed over a portion of the base member, with the ends of the sling support member being secured to respective portions of the base member, so that the sling support member is oriented upward and away from the base member, e.g., extending in a plane oriented at an acute angle to the plane of the base member.

The sling wall member is supported between a portion of the base member and a portion of the sling member so that it forms a portion, e.g., an arcuate wall, of the periphery of the pessary.

When the pessary is in place the arcuate sling wall presses against the inter-vaginal wall, thereby gently closing the urethra. At the same time the ring base member provides support for the uterus, preventing further migration thereof, e.g., further prolapse.

In accordance with a preferred embodiment of the invention the pessary is collapsible to facilitate insertion and removal. In particular, the base member is flexible to be able to be bent or folded with respect to the plane thereof, thereby "collapsing" the base member. The sling support member is also formed of a flexible material to enable it to be bent with respect to the portion of the base member over which it is disposed to "collapse" it. The sling wall is also formed of a flexible material to enable it to be bent or folded when the sling support member is collapsed.

When the pessary is folded or collapsed it can be readily inserted into the vagina to the desired position, whereupon it is released. The release of the pessary enables it to automatically spring back or return to its original or uncollapsed shape to effect the desired anatomical control. Removal of the pessary can be readily accomplished by merely collapsing it in place and then withdrawing it from the vagina.

DESCRIPTION OF THE DRAWINGS

Other objects an d many attendant features of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
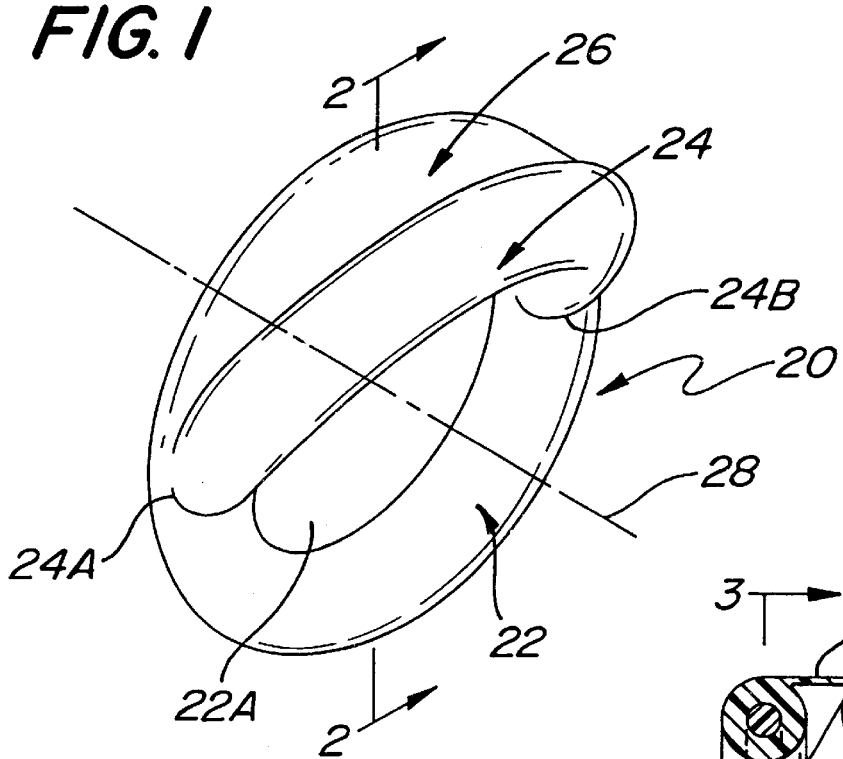
FIG. 1 is an isometric view of one embodiment of a pessary constructed in accordance with this invention.
Figure 4:
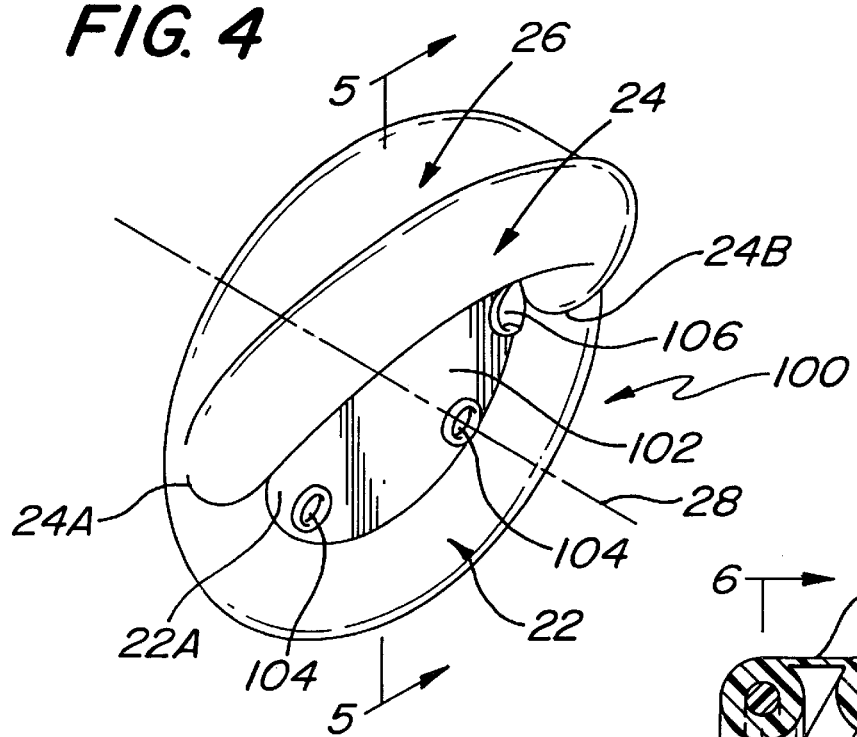
FIG. 4 is an isometric view of an alternative embodiment of a pessary constructed in accordance with this invention.

Referring now to various figures of the drawing where like reference numerals refer to like parts there is shown at 20 in FIG. 1, one embodiment of a vaginal pessary constructed in accordance with this invention. The pessary 20 is of a generally ring-like construction and is arranged for disposition within the vagina for treating a minor (e.g., first or mild second degree) of uterine prolapse and/or stress urinary incontinence while enabling intercourse without discomfort. Thus, the pessary 20 is of particular utility for sexually active women suffering from minor uterine prolapse and/or urinary stress incontinence. In FIG. 4 there is shown an alternative embodiment 100 of a pessary of this invention. The pessary 100 is similar in almost all respects to the pessary 20 except that it includes additional support means (to be described later) so that it can be used to provide relief or treat a greater, e.g., third degree, of uterine prolapse than pessary 20. The additional support means of pessary 100, however, renders the pessary unsuitable for use during sexual activity. Thus, the pessary 100 is particularly suitable for the elderly suffering from greater uterine prolapse and/or stress urinary incontinence.

Each pessary 20 and 100 is arranged to be inserted past the cervix, into the posterior fornix, and past the introitus to an operative position so that it is located in a position to support the bladder and covering the urethra. Moreover, each pessary 20 and 100 is constructed so that it can be collapsed or folded to a compacted configuration. Thus, when it is in the compact or folded configuration it is ready insertion into the vagina to the operative position, at which time it can be "released" to reassume its normal or uncompacted configuration and then oriented to a desired or "operative" orientation. Removal of the pessary merely requires collapsing it in place so that it is once again in its compact orientation, at which time it can be readily removed from the vagina.

Figure 2:
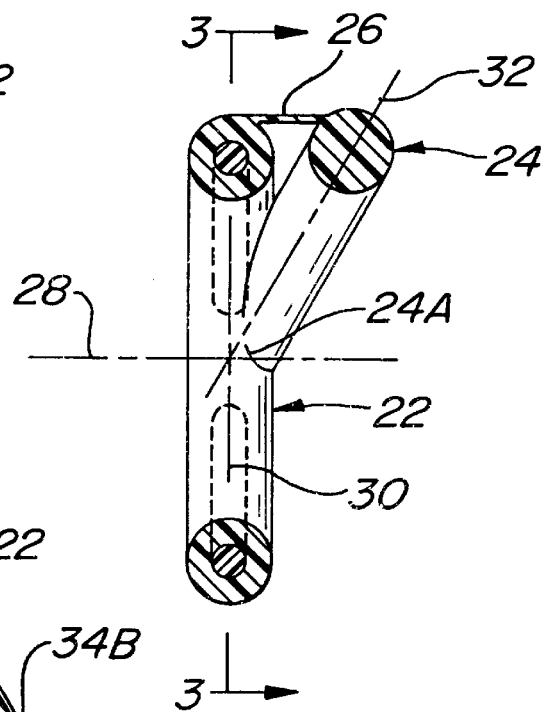
FIG. 2 is a sectional view taken along line 2—2 of FIG. 1.
Figure 3:
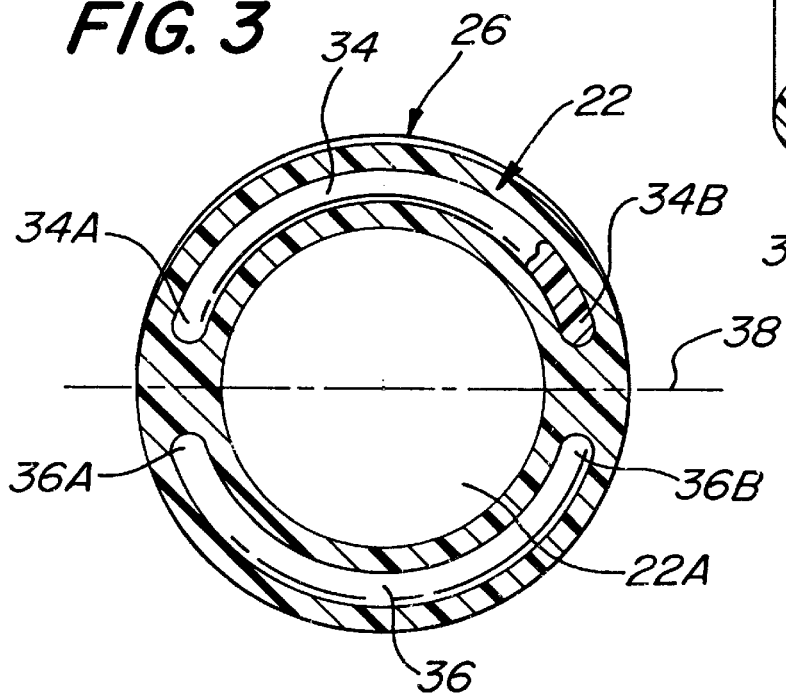
FIG. 3 is a sectional view taken along line 3—3 of FIG. 2.

As can be seen in FIGS. 1–3 the pessary 20 basically comprises a base ring 22, a sling support strut 24 and a sling wall 26. The base ring is of circular annular shape extending about a central axis 28 and lies in or defines a plane 30 which is perpendicular to the central axis 28 (See FIG. 3). The center of the ring 22 is open at 22A. The sling support strut 24 basically comprises approximately half of an annular ring of the same basic dimensions as the base ring. Thus, the strut 24 is arcuate in shape and includes a pair of ends 24A and 24B. The ends 24A and 24B of the strut 24 are fixedly secured to the base ring 22 at diametrically opposed positions and the strut is oriented so that it lies in a plane 32 (FIG. 3) extending at an acute angle, e.g., thirty three degrees, to the plane 30 of the base ring. The sling wall 26 basically comprises a thin membrane secured to and extending between the other periphery of the sling support strut 24 and the portion 22B of the base ring over which the sling support strut.

In accordance with a preferred embodiment of this invention the base ring 22, the sling support strut 25, and the sling membrane or wall 26 are constructed of any suitable resilient biocompatible material, e.g., medical grade silicone, and are preferably formed, e.g., molded, as an integral unit. The medical grade silicone is sufficiently flexible to enable the pessary to be bent or folded, as will be described later, while being sufficiently rigid to provide the desired support. The pessary can be constructed in various sizes. One particular size is that the base ring has an inner diameter of 1.812 inches (4.6 cm) and an outer diameter of 2.75 inches (6.98 cm). The ring thickness is half the difference between the outer and inner ring diameters or 0.47 inches (11.94 cm). The sling membrane or wall has a thickness of 0.03 inches (0.76 mm).

In order to provide mechanical integrity for the pessary and to provide additional rigidity or support for the base ring, a pair of identical arcuate cores or inserts 34 and 36 are located within the base ring 22. The inserts are formed of any suitable material, e.g., stainless steel or medical grade plastic, which is stiffer than the material forming the ring member 22. Each of the inserts is of arcuate shape having a pair of ends. In particular, the insert 34 includes a pair of ends 34A and 34B, whereas the insert 36 includes a pair of ends 36A and 36B. The radius of curvature of each of the inserts 34 and 36 is the same as that of the base ring 22, and each extends for slightly less than 180 degrees. As can be seen clearly in FIG. 3 the inserts 34 and 36 are located within the base ring 22 so that their respective ends 34A and 36A and 34B and 36B are spaced from each other at the diametrically opposed junctions or portions of the base ring to which the end portions of the support strut are connected. The spacing between the inserts enables the base ring to be bent or folded along the line 38 (FIG. 3) connecting the junctions. This enables the pessary to be folded or collapsed into a crescent shaped configuration.

In accordance with the preferred embodiment of this invention the durometer of the silicone making up the pessary is controlled for a mechanical firmness or stiffness of 44 A0 which maintains the desired pessary shape but allows complete flexibility along the intersection line 38. Thus, if the pessary is grasped between the forefinger and thumb on the perimeter ninety degrees (90°) removed from the intersection line 38 and pressure applied, the pessary will easily fold therealong. Moreover, if the upper half ring (sling support strut 24) is included, not only will the base ring 22 fold, but the membrane sling 26 can be simultaneously collapsed. When released, the pessary will automatically assume its original shape shown in FIGS. 1–3.

Figure 7:
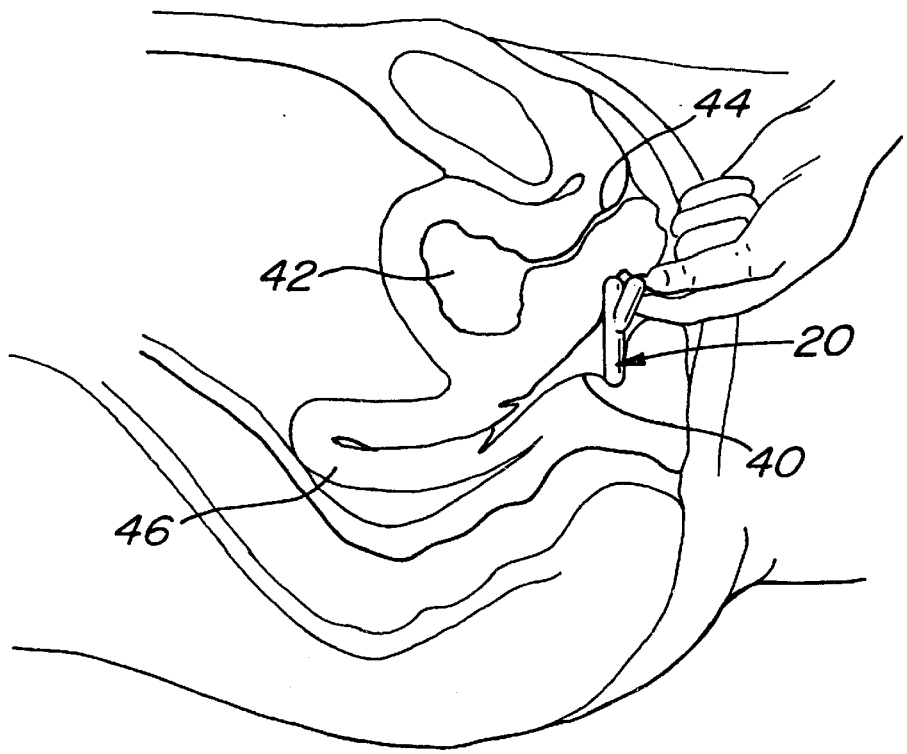
FIG. 7 is an illustration of a portion of the interior of a woman's body showing a pessary of either FIGS. 1 or 4 in the process of being placed in position within the vagina of a woman.
Figure 8:
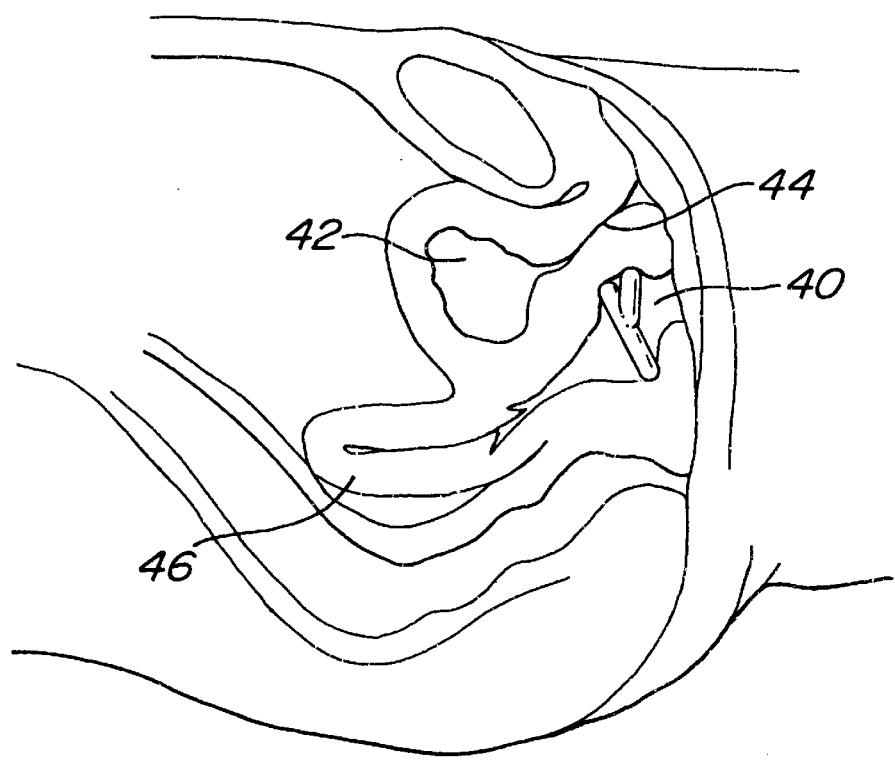
FIG. 8 is an illustration like that of FIG. 7 but showing the pessary of either FIGS. 1 or 4 in its fully operative position.

Once the pessary is collapsed into the crescent shape as just described it is ready for insertion into the vagina as shown in FIGS. 7 and 8. To that end the collapsed, e.g., crescent shaped, pessary 20 is inserted into the vagina 40, past the cervix and into the posterior fornix. Once the pessary has passed the introitus, the pessary is released to enable it to flex back or expand to its normal shape shown in FIG. 1. Then with the index finger, the expanded pessary is given a quarter turn so that the sling membrane wall 26 is positioned to support the bladder 42 and covering the urethra 44, as shown in FIG. 7. The hand is then removed, leaving the pessary in place, like shown in FIG. 8. In this position the membrane wall 26 of the pessary is aligned to support the bladder while the thirty three degree elevated sling support strut provides additional support for the bladder neck. Thus, gentle pressure is applied by the sling membrane to close the urethra 44, thereby preventing involuntary leakage of urine from the bladder 42. The base ring portion which is located opposite the sling support and sling membrane automatically extends within the vaginal cavity providing additional lateral support to maintain the positional integrity of the entire pessary. Moreover, the base ring 22 provides support for the uterus 46 to prevent further distension or dropping (prolapse).

A physician should be able to insert an examining finger between the outer rim of the pessary and the vaginal wall. This spacing will insure the patient's comfort and virtually eliminate the risk of pressure necrosis.

Once in place, the pessary should not dislodge by either standing, sitting, squatting or bearing down and it should not be uncomfortable for the patient during these normal routine activities, including sexual intercourse.

The pessary is easily removed for cleaning by simply using a finger to begin the folding process and then the thumb to complete the folding of it to its compact configuration. In particular, when the pessary is to be removed, a finger should be wrapped around the back portion of the base ring, i.e., that portion opposite the membrane wall 26, and downward pressure applied. This motion will begin the folding process of the pessary and by extending the finger just a bit further, the membrane sling supported by the support strut can be easily collapsed. The pessary is now collapsed and ready to be extracted from the vagina.

Figure 5:
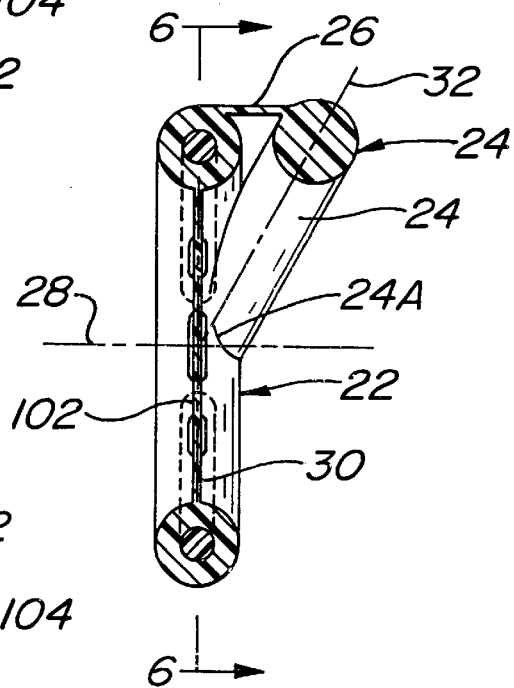
FIG. 5 is a sectional view taken along line 5—5 of FIG. 4.
Figure 6:
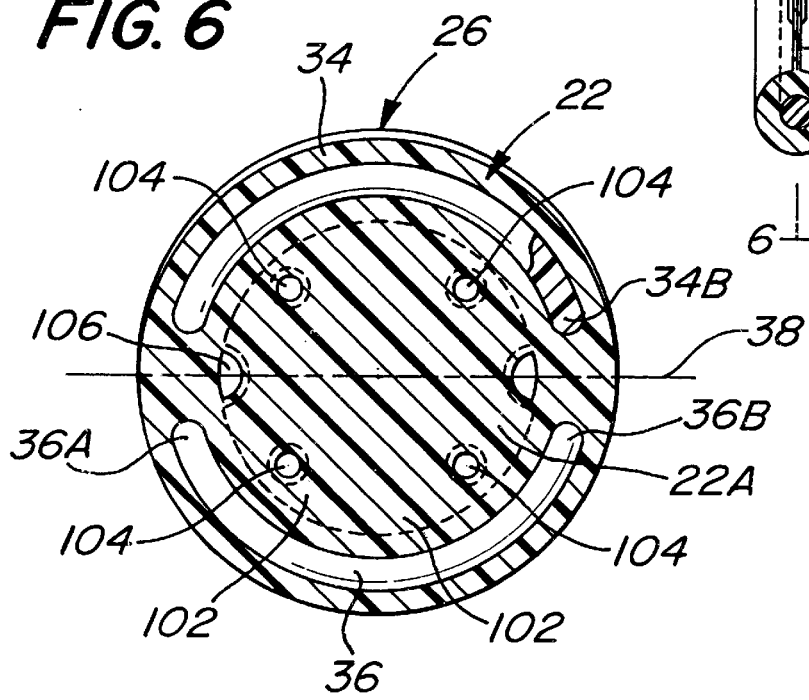
FIG. 6 is a sectional view taken along line 6—6 of FIG. 5.

If greater support is required, e.g., for treatment of third degree uterine prolapse, the pessary 100 of FIGS. 4–6 is indicated. That pessary is identical in construction to pessary 20 except for the inclusion of an additional support wall or membrane, to be described hereinafter. In the interests of brevity the common components of the pessary 100 to the pessary 20 will be given the same reference numerals and a description of such components will not be reiterated.

Turning now to FIGS. 4–6 it can be seen that the pessary 100 includes a second wall or membrane 102 covering the opening 22A in the base ring. The membrane wall 102 is formed of a resilient material, e.g., the same silicone material, as making up the base ring, and is preferably formed, e.g., molded, as an integral unit therewith. The inclusion of the wall 102 serves to strengthen the base ring so that it is more resistant to collapse than the base ring 22 of the pessary 20. However, since the wall 102 closes the opening 22A in the base ring, intercourse with the pessary 100 in place is precluded. The membrane or wall 102 include plural, e.g., four, openings 104, therein to enable fluids to pass therethrough. A pair of diametrically opposed openings 106 are provided in the second wall or membrane 102 along the fold line or axis 38 to ensure that the pessary 102 can still be freely folded along that line, notwithstanding the additional presence of the wall 102.

Insertion, use, and removal of the pessary 100 is the same as described with respect to pessary 20, and hence will not be reiterated herein.

As should be appreciated from the foregoing discussion the unique design of the subject pessaries permits adequate support of the cystocele, as well as simultaneous correction of stress incontinence. Other known pessaries that are readily available are inadequate or deficient in design to effectively counteract these maladies. The subject pessaries, possessing a support or sling membrane for bladder and upper bladder support also creates less pressure on the bladder neck since they elevate the cystocele at the same time.

In summary the subject pessaries can be used to control uterine prolapse and/or relieve urinary stress incontinence, they can be easily inserted and removed, they can be manufactured readily in various sizes, they can be autoclaved (if necessary) for clinical sterilization, they can be easily cleaned by the patient daily with a mild soap and water, and they should exhibit a relatively long and useful life. Moreover, embodiment of pessaries constructed in accordance with this invention and which do not include the additional support membrane or wall closing the opening in the center of the base ring can be comfortably used by a sexually active patient.

It should be pointed out at this juncture that while the foregoing has described the subject pessaries in the context of use to treat uterine prolapse and/or urinary stress incontinence, it is clear that the subject pessaries can be used for other medical purposes wherein internal anatomical support and/or minor pressure application is desired.

Without further elaboration the foregoing will so fully illustrate our invention that others may, by applying current or future knowledge, adapt the same for use under various conditions of service.

We claim:

1. A pessary for treating uterine prolapse and/or stress urinary incontinence, said pessary being formed of a biocompatible material comprising:

(a) a base member in the form of a ring defining a first plane, said base member including a flexible portion to enable it to be bent along a predetermined line in said first plane, but resistant to bending elsewhere, (b) a sling support member in the form of an arcuate portion of a ring and having a pair of ends, said sling support member being disposed over a portion of said base member and defining as second plane oriented upward and away from said first plane at an acute angle, said ends of said sling support member being secured to respective portions of said base member, and (c) a sling wall formed of a thin membrane and being supported between a portion of said base member and a portion of said sling support member, said sling wall forming a portion of the periphery of said pessary.

2. The pessary of claim 1 wherein said pessary is constructed so that said sling support member and the portion of said base member over which said sling support member is disposed are movable relative to each other.

3. The pessary of claim 2 wherein said sling support member is flexible to enable said portion of said base member and said sling support member to be bent with respect to each other.

4. The pessary of claim 1 wherein said pessary is constructed so that said sling support member and said portion of said base member over which said sling support member is disposed are movable relative to each other.

5. The pessary of claim 4 wherein said sling support member is flexible to enable said portion of said base member and said sling support member to be bent with respect to each other.

6. The pessary of claim 1 wherein said acute angle is approximately thirty three degrees.

7. The pessary of claim 1 wherein said thin membrane is formed of a flexible material.

8. The pessary of claim 1 wherein said base member, said sling support member, and said sling wall are each formed of a flexible material to enable said base member to be bent or folded with respect to the plane thereof and to enable said sling support member to be bent with respect to said portion of said base member over which said sling support member is disposed.

9. The pessary of claim 8 wherein said base member includes a pair of strengthening inserts, each of said inserts being an arcuate shaped member having a pair of ends, said inserts being located within said base member so that the ends of one of said inserts are spaced from the corresponding ends of the other of said inserts, whereupon said base member can be bent or folded with respect to the plane thereof along a line between the spaced ends of said inserts.

10. The pessary of claim 9 additionally comprising a stiffening wall member fixedly secured to said base member and extending in the plane of said base member.

11. The pessary of claim 10 wherein said base member and said stiffening wall member are each flexible to enable said base member and said stiffening wall member to be able to be bent or folded with respect to the plane thereof.

12. A pessary for treating uterine prolapse and/or stress urinary incontinence, said pessary being formed of a biocompatible material comprising:

(a) a base member in the form of a ring defining a plane and being formed of a flexible material to be able to be bent with respect to said plane, and wherein said base member includes a pair of strengthening inserts, each of said inserts being an arcuate shaped member having a pair of ends, said inserts being located within said base member so that the ends of one of said inserts are spaced from the corresponding ends of the other of said inserts, whereupon said base member can be bent or folded with respect to said plane along a line between the spaced ends of said inserts, (b) a sling support member in the form of an arcuate portion of a ring and having a pair of ends, said sling support member being disposed over a portion of said base member, with said ends of said sling support member being secured to respective portions of said base member and with said sling support member being oriented to extend upward and away from the plane of said base member, and (c) a sling wall supported between a portion of said base member and a portion of said sling support member, said sling wall forming a portion of the periphery of said pessary.

13. The pessary of claim 12 wherein said sling member is formed of a flexible material to enable said sling support member to be bent with respect to said portion of said base member over which said sling support member is disposed.

14. The pessary of claim 13 wherein said sling support member and said base member of formed of the same material.

15. The pessary of claim 13 additionally comprising a stiffening wall member fixedly secured to said base member and extending in the plane of said base member.

16. The pessary of claim 15 wherein said base member and said stiffening wall member are each flexible to enable said base member and said stiffening wall member to be able to be bent or folded with respect to the plane thereof.

17. A pessary for treating uterine prolapse and/or stress urinary incontinence, said pessary being formed of a biocompatible material comprising:

(a) a base member in the form of a ring defining a plane, (b) a stiffening wall member fixedly secured to said base member and extending in the plane of said base members, (c) a sling support member in the form of an arcuate portion of a ring and having a pair of ends, said sling support member lying in a plane and being disposed over a portion of said base member, with said ends of said sling support member being secured to respective portions of said base member and with the plane of said sling support member being oriented to extend upward and away from the plane of said base member, and (d) a sling wall supported between a portion of said base member and a portion of said sling support member, said sling wall forming a portion of the periphery of said pessary.

18. The pessary of claim 17 wherein said base member and said stiffening wall member are each flexible to enable said base member and said stiffening wall member to be able to be bent or folded with respect to the plane thereof.

* * * * *